United States Patent
Ogura et al.

(10) Patent No.: US 6,712,768 B2
(45) Date of Patent: Mar. 30, 2004

(54) AUGMENTATION-INDEX DETERMINING APPARATUS AND ARTERIOSCLEROSIS INSPECTING APPARATUS

(75) Inventors: Toshihiko Ogura, Komaki (JP); Kiyoyuki Narimatsu, Komaki (JP); Akira Tampo, Komaki (JP); Takashi Honda, Komaki (JP)

(73) Assignee: Colin Corporation, Komaki (JP)

( * ) Notice: Subject to any disclaimer, the term of this patent is extended or adjusted under 35 U.S.C. 154(b) by 8 days.

(21) Appl. No.: 10/237,099

(22) Filed: Sep. 9, 2002

(65) Prior Publication Data
US 2003/0130583 A1 Jul. 10, 2003

(30) Foreign Application Priority Data
Jan. 10, 2002 (JP) ........................................ 2002-003403

(51) Int. Cl.⁷ ................................................ A61B 5/02
(52) U.S. Cl. ........................ 600/494; 600/490; 600/495
(58) Field of Search ............................... 600/490, 492, 600/493, 494, 495, 496, 500, 501, 502, 481, 485

(56) References Cited

U.S. PATENT DOCUMENTS 6,283,922 B1    9/2001  Goto et al.
6,612,993 B2 *  9/2003  Narimatsu .................. 600/500

FOREIGN PATENT DOCUMENTS

WO    WO 90/11043    10/1990

* cited by examiner

Primary Examiner—Max F. Hindenburg
Assistant Examiner—Navin Natnithithadha
(74) Attorney, Agent, or Firm—Oliff & Berridge, PLC

(57) ABSTRACT

An augmentation-index determining apparatus, including a cuff, a cuff-pressure changing device which changes a pressing pressure of the cuff, a pulse-wave extracting device which extracts a pulse wave from the cuff, a peak-occurrence-time determining device for determining, based on a high-cuff-pressure pulse wave which is extracted by the pulse-wave extracting device when the cuff-pressure changing device makes the pressing pressure of the cuff higher than a systolic blood pressure of a subject, a time of occurrence of a peak point of an incident-wave component of the high-cuff-pressure pulse and a time of occurrence of a peak point of a reflected-wave component of the high-cuff-pressure pulse wave, and an augmentation-index determining device for determining, based on the respective times of occurrence of the respective peak points of the incident-wave and reflected-wave components of the high-cuff-pressure pulse, respective times of occurrence of respective peak points of incident-wave and reflected-wave components of a low-cuff-pressure pulse which is extracted by the pulse-wave extracting device when the cuff-pressure changing device makes the pressing pressure of the cuff lower than a mean blood pressure of the subject, and determining an augmentation index based on respective magnitudes of the low-cuff-pressure pulse wave at the respective times of occurrence of the respective peak points of the incident-wave and reflected-wave components of the low-cuff-pressure pulse.

8 Claims, 5 Drawing Sheets

AUGMENTATION-INDEX DETERMINING APPARATUS AND ARTERIOSCLEROSIS INSPECTING APPARATUS

BACKGROUND OF THE INVENTION

1. Field of the Invention

The present invention relates to an augmentation-index determining apparatus which determines an augmentation index of a living subject, and an arteriosclerosis inspecting apparatus which inspects arteriosclerosis of a living subject based on an augmentation index of the subject.

2. Related Art Statement

Augmentation index, generally known as AI, indicates a proportion of a reflected-wave component of a pulse wave to an incident-wave component of the same, and is used to evaluate compliance of aorta. The greater the compliance is, the smaller the reflected-wave component is, and the smaller the compliance is, the greater the reflected-wave component is. That is, the harder the aorta is, the greater the reflected-wave component of the aortic pulse wave is. Thus, the augmentation index indicates arteriosclerosis and accordingly is used as an index to examine or inspect it.

As described above, augmentation index represents a proportion of a reflected-wave component of a pulse wave to an incident-wave component of the same. However, since it is difficult to completely separate a detected pulse wave into an incident-wave component and a reflected-wave component, an augmentation index is determined by first identifying respective times of occurrence of respective peak points of the incident-wave and reflected-wave components of the detected pulse wave, and then dividing a difference between respective magnitudes of the detected pulse wave at the respective times of occurrence of the respective peak points of the incident-wave and reflected-wave components, by a pulse pressure of the detected pulse wave. A time of occurrence of an inflection point or a maximal point of the detected pulse wave between a rising point and a peak point of a heartbeat-synchronous pulse of the detected pulse wave is identified as the time of occurrence of the peak point of the incident-wave component; a time of occurrence of the first or earliest maximal point of the heartbeat-synchronous pulse of the detected pulse wave, subsequent to the peak point of the incident-wave component, is identified as the time of occurrence of the peak point of the reflected-wave component; and a difference between the greatest and smallest magnitudes of the heartbeat-synchronous pulse of the detected pulse wave is determined as the pulse pressure of the detected pulse wave.

As described above, augmentation index is used to evaluate compliance of aorta. To this end, clinically, augmentation index is determined based on a carotid pulse wave that is detected from carotid artery that is the nearest to the aorta of all the arteries from which pulse waves can be non-invasively detected.

However, skill is needed to wear a carotid-pulse-wave sensor at an appropriate position to detect a carotid pulse wave, and a considerably long time is needed to detect it. Thus, there has been a demand to determine augmentation index based on a more easily detectable pulse wave, such as a brachial artery.

However, it has been elucidated that regarding the other sorts of pulse waves than the carotid pulse wave, there are some cases where a time of occurrence of a peak point of a reflected-wave component does not correspond to the earliest maximal point subsequent to a peak point of an incident-wave component.

Each of FIGS. 1A and 1B shows, regarding a corresponding one of two patients, a carotid pulse wave and a brachial pulse wave that are simultaneously detected from the one patient and respective rising points of which are aligned with each other. The brachial pulse wave is extracted from pressure oscillation that is transmitted to a cuff in a state in which a pressure of the cuff is lower than a diastolic blood pressure of the patient (in this specification, this pulse wave will be referred to as the "low-cuff-pressure pulse wave"). This is a common method to detect an accurate pulse wave.

Regarding the case shown in FIG. 1A, a time, t1, of occurrence of a peak point of an incident-wave component and a time, t2, of occurrence of a peak point of a reflected-wave component, each determined on a brachial pulse wave, coincide with those determined on a carotid pulse wave. In many cases, this is true.

On the other hand, regarding the case shown in FIG. 1B, a time t1 of occurrence of a peak point of an incident-wave component determined on a brachial pulse wave coincides with that determined on a carotid pulse wave. However, a time t3 of occurrence of a peak point of a reflected-wave component of the brachial pulse wave, i.e., a time of occurrence of the earliest maximal point subsequent to the peak point of the incident-wave component, does not coincide with a time t2 of occurrence of a peak point of a reflected-wave component of the carotid pulse wave. Therefore, if an augmentation index is determined based on the brachial pulse wave shown in FIG. 1B in the conventional method, then the index is not accurate.

SUMMARY OF THE INVENTION

It is therefore an object of the present invention to provide an augmentation-index determining apparatus which can determine an augmentation index with high accuracy.

The Inventors have found that pressure oscillation occurring to a cuff in a state in which a pressure of the cuff is higher than a systolic blood pressure of a living subject has two maximal points, as will be described later in connection with FIGS. 4A and 4B, and that the first maximal point corresponds to a peak point of an incident-wave component and the second maximal point corresponds to a peak point of a reflected-wave component. If respective times of occurrence of the respective peak points of the incident-wave and reflected-wave components are used to determine respective times of occurrence of respective peak points of incident-wave and reflected-wave components of a pulse wave detected to determine an augmentation index, then the index can enjoy high accuracy. The present invention has been developed based on this concept.

The above object has been achieved by the present invention. According to the present invention, there is provided an apparatus for determining, based on a pulse wave detected from a living subject, an augmentation index indicating a proportion of a reflected-wave component of the pulse wave to an incident-wave component thereof, the apparatus comprising an inflatable cuff which is adapted to be worn on a portion of the subject and inflated to apply a pressing pressure to the portion; a cuff-pressure changing device which changes the pressing pressure of the cuff; a pulse-wave extracting device which extracts a pulse wave from a pressure oscillation which is transmitted from the portion of the subject to the cuff; a peak-occurrence-time determining means for determining, based on a high-cuff-pressure pulse wave which is extracted by the pulse-wave extracting device when the cuff-pressure changing device makes the pressing pressure of the cuff higher than a systolic blood pressure of the portion of the subject, a time of occurrence of a peak point of an incident-wave component of the high-cuff-pressure pulse and a time of occurrence of a peak point of a reflected-wave component of the high-cuff-pressure pulse wave; and an augmentation-index determining means for determining, based on the respective times of occurrence of the respective peak points of the incident-wave and reflected-wave components of the high-cuff-pressure pulse, determined by the peak-occurrence-time determining means, respective times of occurrence of respective peak points of incident-wave and reflected-wave components of a low-cuff-pressure pulse which is extracted by the pulse-wave extracting device when the cuff-pressure changing device makes the pressing pressure of the cuff lower than a mean blood pressure of the portion of the subject, and determining an augmentation index based on respective magnitudes of the low-cuff-pressure pulse wave at the respective times of occurrence of the respective peak points of the incident-wave and reflected-wave components of the low-cuff-pressure pulse.

According to this invention, the peak-occurrence-time determining means determines, based on the pulse wave detected when the pressing pressure of the cuff is higher than the systolic blood pressure of the subject, the respective times of occurrence of the respective peak points of the incident-wave and reflected-wave components of the pulse wave, and the augmentation-index determining means determines, based on the respective times of occurrence of the respective peak points of the incident-wave and reflected-wave components, determined by the peak-occurrence-time determining means, the respective times of occurrence of the respective peak points of the incident-wave and reflected-wave components of the low-cuff-pressure pulse, and determines the augmentation index based on the respective magnitudes of the low-cuff-pressure pulse wave at the respective times of occurrence of the respective peak points of the incident-wave and reflected-wave components of the low-cuff-pressure pulse. The thus determined augmentation index enjoys a high accuracy.

According to a preferred feature of the present invention, the cuff is adapted to be worn on an upper arm of the subject, the augmentation-index determining means determines the augmentation index based the high-cuff-pressure pulse wave and the low-cuff-pressure pulse wave each of which is extracted by the pulse-wave extracting device from the pressure oscillation transmitted from an artery of the upper arm to the cuff worn on the upper arm.

According to another preferred feature of the present invention, the cuff-pressure changing device decreases, in a blood-pressure measuring operation, the pressing pressure of the cuff from a pressure higher than the systolic blood pressure of the portion of the subject, to a pressure lower than a diastolic blood pressure of the portion of the subject, the pulse-wave extracting device extracts the high-cuff-pressure pulse wave when the cuff-pressure changing device makes, in the blood-pressure measuring operation, the pressing pressure of the cuff higher than the systolic blood pressure of the portion of the subject, and the pulse-wave extracting device extracts the low-cuff-pressure pulse wave when the cuff-pressure changing device makes, in the blood-pressure measuring operation, the pressing pressure of the cuff lower than the diastolic systolic blood pressure of the portion of the subject.

According to this feature, when the pressing pressure of the cuff is changed in the blood-pressure measuring operation, the high-cuff-pressure pulse wave and the low-cuff-pressure pulse wave are obtained, and the augmentation index is determined based on the high-cuff-pressure and low-cuff-pressure pulse waves. Thus, the augmentation index can be obtained concurrently with the blood-pressure measuring operation.

The above-indicated augmentation-index determining apparatus may be used as an arteriosclerosis inspecting apparatus. That is, according to another preferred feature of the present invention, there is provided an apparatus for inspecting arteriosclerosis of the living subject, based on the augmentation index determined by the augmentation-index determining apparatus.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1A:
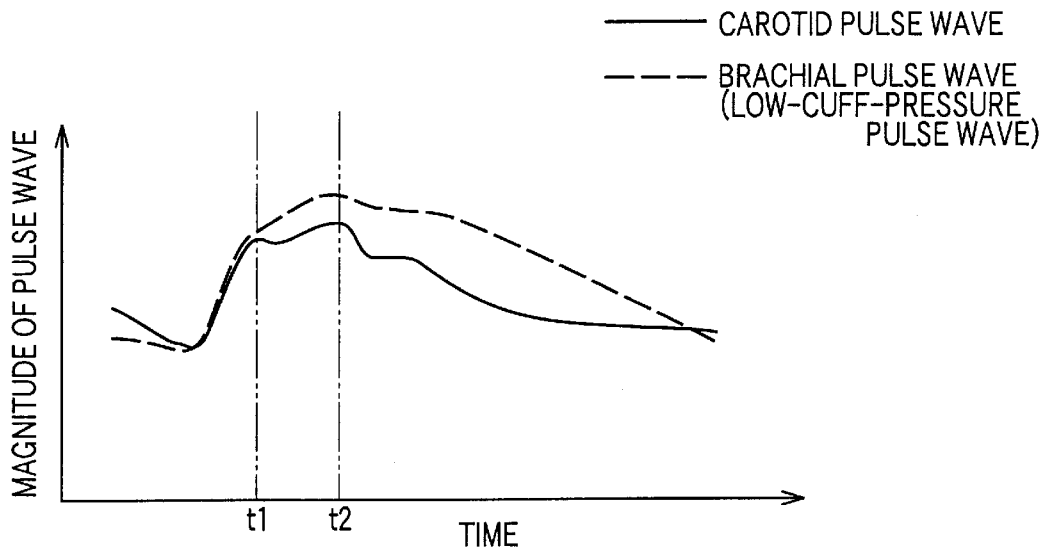
FIG. 1A is a view showing a carotid pulse wave and a brachial pulse wave which are detected from a patient, such that respective rising points of the two pulse waves are intentionally aligned with each other.
Figure 1B:
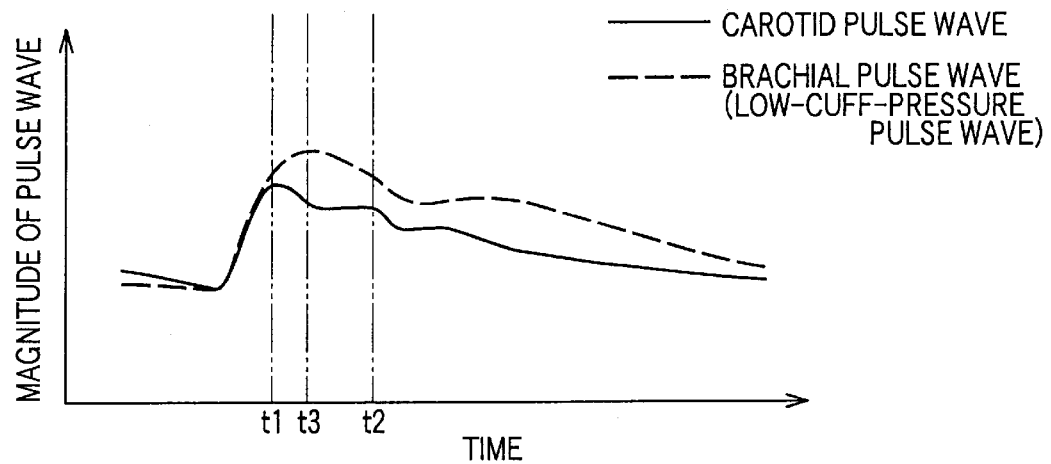
FIG. 1B is a view showing a carotid pulse wave and a brachial pulse wave which are detected from another patient, such that respective rising points of the two pulse waves are intentionally aligned with each other.

Hereinafter, there will be described an embodiment of the present invention in detail by reference to the drawings. FIG. 1 is a diagrammatic view showing a circuitry of an arteriosclerosis inspecting apparatus 10 to which the present invention is applied.

Figure 2:
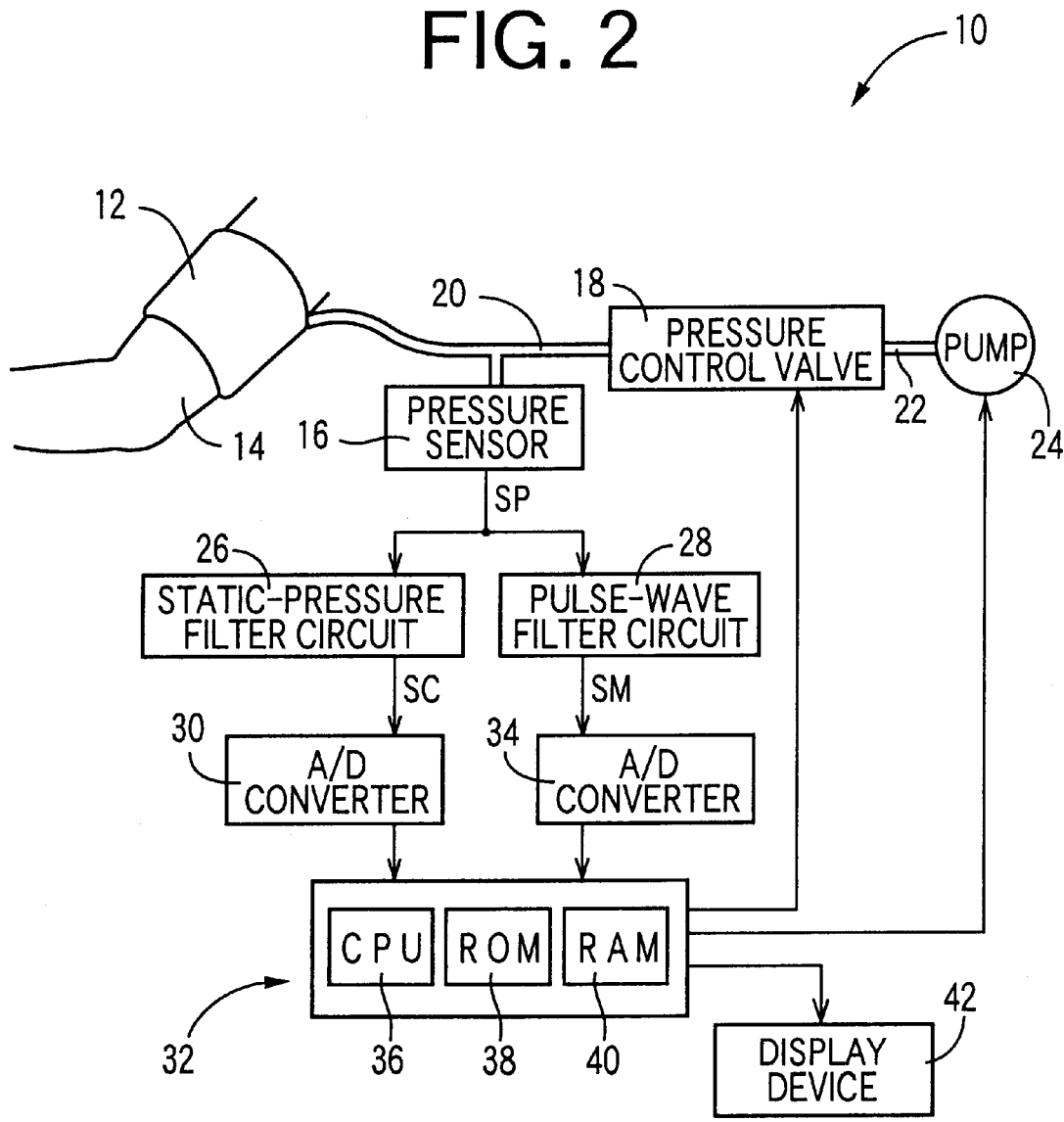
FIG. 2 is a diagrammatic view showing a circuitry of an arteriosclerosis inspecting apparatus to which the present invention is applied.

In FIG. 2, reference numeral 12 designates an inflatable cuff which includes a belt-like cloth bag and a rubber bag accommodated in the cloth bag and which is adapted to be wound around an upper arm 14 of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit (i.e., a pulse-wave extracting device) 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter 30. The pulse-wave filter circuit 28 includes a band-pass filter which extracts, from the pressure signal SP, a cuff-pulse-wave signal, SM, representing a cuff pulse wave as an oscillatory component of the detected air pressure that has prescribed frequencies. The filter circuit 28 supplies the cuff-pulse-wave signal SM to the control device 32 via an A/D converter 34. The cuff pulse wave represented by the cuff-pulse-wave signal SM is a pressure oscillation which is produced by a brachial artery, not shown, of the patient and is transmitted to the cuff 12.

The control device 32 is provided by a so-called microcomputer including a CPU (central processing unit) 36, a ROM (read only memory) 38, a RAM (random access memory) 40, and an I/O (input-and-output) port, not shown. The CPU 36 processes signals according to the control programs pre-stored in the ROM 38 by utilizing the temporary-storage function of the RAM 40, and supplies drive signals via the I/O port to the air pump 24 and the pressure control valve 18 so as to control the cuff pressure PC. Moreover, the CPU 36 determines a pulse-wave augmentation index AI, as will be described below in connection with the control functions illustrated in detail in FIG. 3, and controls what is displayed by a display device 42.

Figure 3:
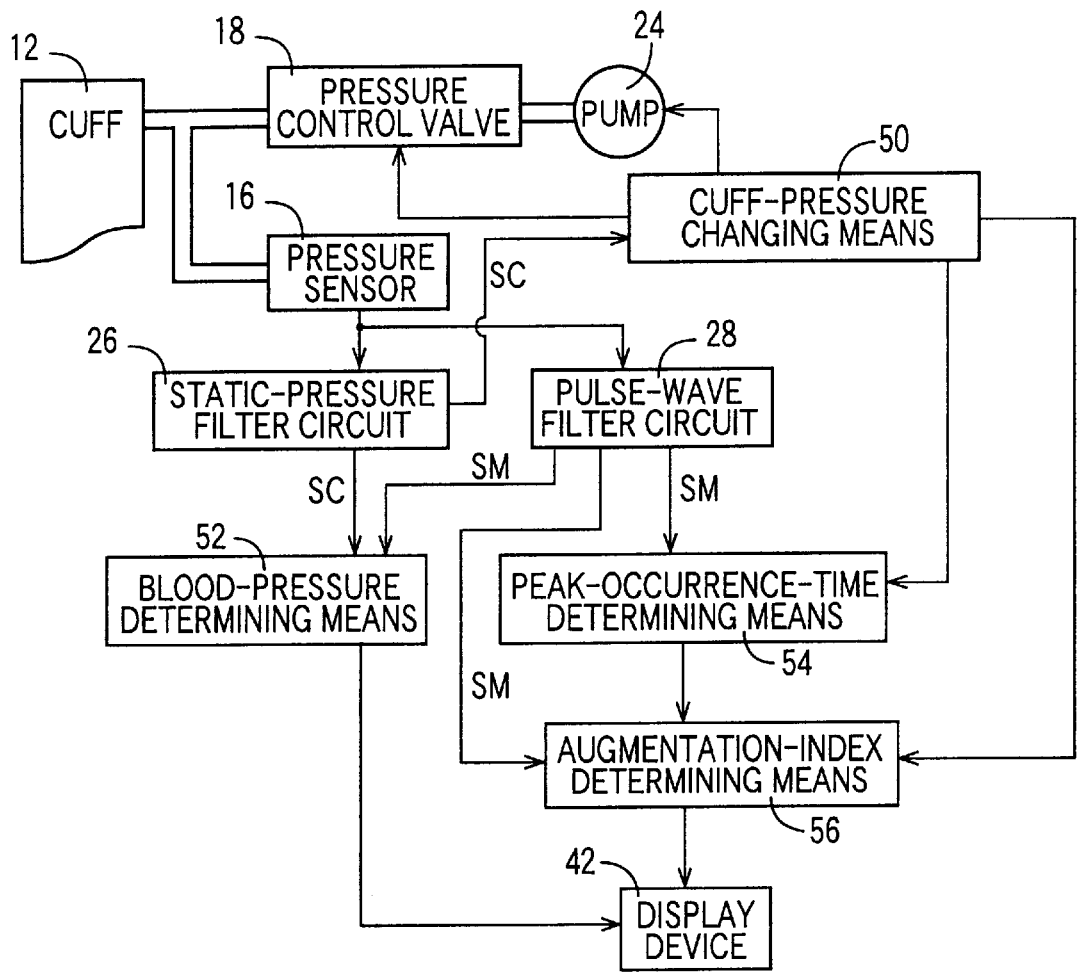
FIG. 3 is a block diagram for explaining essential control functions of an electronic control device of the apparatus of FIG. 2.

FIG. 3 is a block diagram for explaining the essential control functions of the control device 32 of the arteriosclerosis inspecting apparatus 10.

A cuff-pressure changing means 50 operates, based on the cuff-pressure signal SC supplied from the static-pressure filter circuit 26, the pressure control valve 18 and the air pump 24 so as to change the cuff pressure PC. Thus, the cuff-pressure changing means 50 cooperates with the static-pressure filter circuit 26, the pressure control valve 18, and the air pump 24 to provide a cuff-pressure changing device 51. The cuff-pressure changing means 50 operates the pressure control valve 18 and the air pump 24, thereby controlling a blood-pressure measuring operation as described below. More specifically described, the cuff-pressure changing means 50 operates for quickly increasing the cuff pressure PC to a prescribed increase-target pressure (e.g., 180 mmHg) that would be higher than a systolic blood pressure $BP_{SYS}$ of the upper arm 14 of the patient and, subsequently, slowly decreasing the cuff pressure PC at a rate of, e.g., 2 or 3 mmHg/sec. After a blood-pressure determining means 52, described below, determines a diastolic blood-pressure value $BP_{DIA}$ of the patient, the cuff-pressure changing means 50 maintains, for more than a time corresponding to one heartbeat of the patient, the cuff pressure PC at a pulse-wave detecting pressure that is determined based on the diastolic blood-pressure value $BP_{DIA}$ determined by the blood-pressure determining means 52, or a mean blood-pressure value $BP_{MEAN}$ that has also been determined by the blood-pressure determining means 52 during the slow decreasing of the cuff pressure PC. The pulse-wave detecting pressure is determined at a pressure lower than the mean blood-pressure value $BP_{MEAN}$, preferably, lower than the diastolic blood-pressure value $BP_{DIA}$, because, when the cuff pressure PC is higher than the diastolic blood-pressure value $BP_{DIA}$, the brachial pulse wave extracted by the pulse-wave filter circuit 28 is more or less deformed, especially, when the cuff pressure PC is higher than the mean blood-pressure value $BP_{MEAN}$, the brachial pulse wave is so largely deformed that an accurate augmentation index AI may not be determined. On the other hand, if the cuff pressure PC is too low, the brachial pulse wave extracted by the pulse-wave filter circuit 28 is too small to determine an accurate augmentation index AI. Thus, the pulse-wave detecting pressure is determined at an appropriate pressure which assures that the brachial pulse wave shows a sufficiently great magnitude.

The blood-pressure determining means 52 determines, based on change of respective amplitudes of successive heartbeat-synchronous pulses of the brachial pulse wave represented by the cuff-pulse-wave signal SM continuously obtained during the slow decreasing of the cuff pressure PC under the control of the cuff-pressure changing means 50, a systolic blood pressure $BP_{SYS}$, the mean blood pressure $BP_{MEAN}$, and the diastolic blood pressure $BP_{DIA}$ of the patient, according to well-known oscillometric method. In addition, the blood-pressure determining means 52 operates the display device 42 to display the thus determined blood-pressure values $BP_{SYS}$, etc.

Figure 4A:
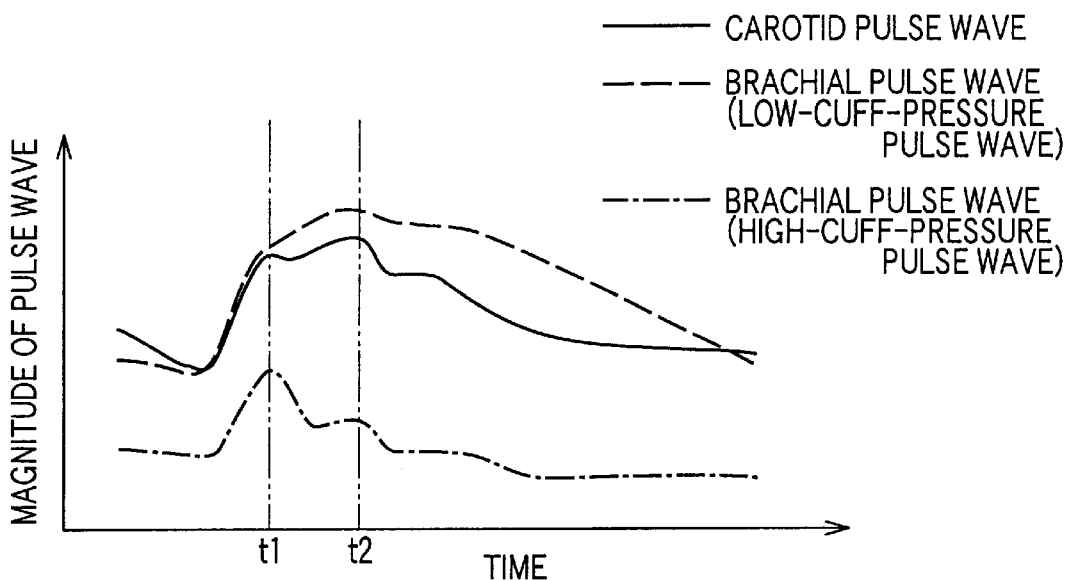
FIG. 4A is a view showing, in addition to the carotid pulse wave and the brachial pulse wave (i.e., low-cuff-pressure pulse wave) shown in FIG. 1A, a high-cuff-pressure pulse wave, such that respective rising points of the three pulse waves are intentionally aligned with each other.
Figure 4B:
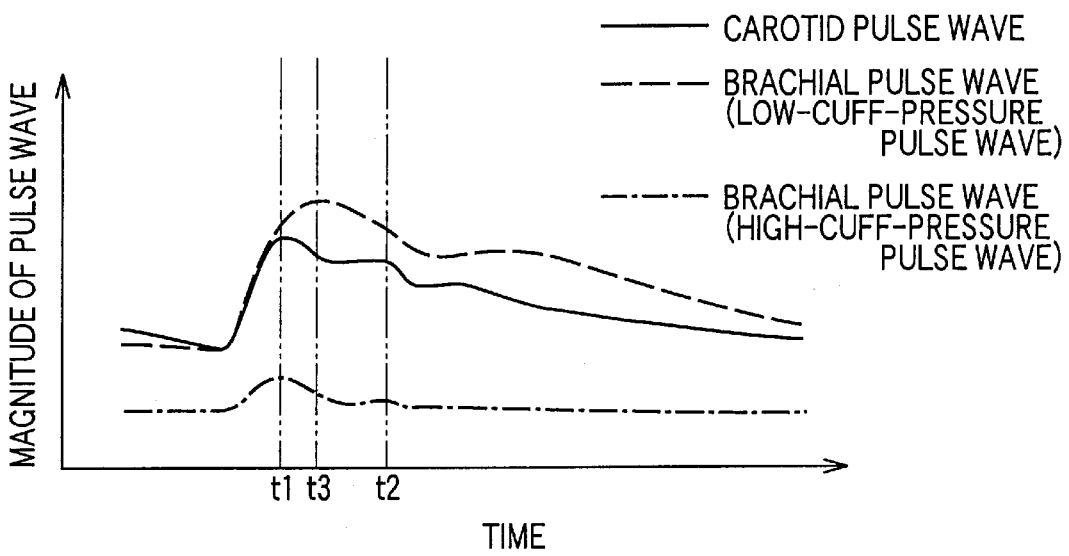
FIG. 4B is a view showing, in addition to the carotid pulse wave and the brachial pulse wave (i.e., low-cuff-pressure pulse wave) shown in FIG. 1B, a high-cuff-pressure pulse wave, such that respective rising points of the three pulse waves are intentionally aligned with each other.

A peak-occurrence-time determining means 54 determines a time of occurrence of a peak point of an incident-wave component, and a time of occurrence of a peak point of a reflected-wave component, each contained in the brachial pulse wave extracted by the pulse-wave filter circuit 28 in a state in which the cuff pressure PC is slowly decreased, by the cuff-pressure changing means 50, in a pressure range higher than the systolic blood-pressure value $BP_{SYS}$ of the upper arm 14 (hereinafter, this brachial artery is referred to as the "high-cuff-pressure pulse wave"). FIGS. 4A and 4B shows the two pulse waves (i.e., carotid pulse wave and low-cuff-pressure pulse wave) shown in FIGS. 1A and 1B, and the high-cuff-pressure pulse wave, such that respective rising points of the three pulse waves are intentionally aligned with each other. The high-cuff-pressure pulse wave is indicated at one-dot-chain line. Both of FIGS. 4A and 4B show that the high-cuff-pressure pulse wave has two peak points. The earlier one of the two peak points coincides with a time, t1, of occurrence of a peak point of an incident-wave component of a carotid pulse wave, and the later one of the two peak points coincides with a time, t2, of occurrence of a peak point of a reflected-wave component of the carotid pulse wave. Therefore, the peak-occurrence-time determining means 54 determines the time of occurrence of the earlier one of the two peak points of the high-cuff-pressure pulse wave, as the time of occurrence of the peak point of the incident-wave component of the brachial artery, and additionally determines the time of occurrence of the later one of the two peak points of the high-cuff-pressure pulse wave, as the time of occurrence of the peak point of the reflected-wave component of the brachial pulse wave.

An augmentation-index determining means 56 first determines, based on the respective times of occurrence of the respective peak points of the incident-wave and reflected-wave components of the brachial artery, each determined by the peak-occurrence-time determining means 54, a time of occurrence of a peak point of an incident-wave component, and a time of occurrence of a peak point of a reflected-wave component, each contained in the brachial pulse wave, i.e., low-cuff-pressure pulse wave, extracted by the pulse-wave filter circuit 28 in a state in which the cuff pressure PC is maintained at the pulse-wave detecting pressure by the cuff-pressure changing means 50. More specifically described, the augmentation-index determining means 56 first aligns respective times of occurrence of respective rising points of the high-cuff-pressure pulse wave and the low-cuff-pressure pulse wave, with each other, and then determines, in this state, the respective times of occurrence of the respective peak points of the incident-wave and reflected-wave components of the high-cuff-pressure pulse wave, as respective times of occurrence of respective peak points of incident-wave and reflected-wave components of the low-cuff-pressure pulse wave. Moreover, the determining means 56 determines a pulse pressure PP of the low-cuff-pressure pulse wave, substitutes, for the following Expression 1, the pulse pressure PP and a difference ΔP (=b−a) obtained by subtracting a magnitude, a, of the low-cuff-pressure pulse wave at the time of occurrence of the peak point of the incident-wave component, from a magnitude, b, of the low-cuff-pressure pulse wave at the time of occurrence of the peak point of the reflected-wave component, so as to determine an augmentation index AI, and operates the display device 42 to display the thus determined index AI:

$$AI=(\Delta P/PP)\times 100 (\%) \qquad \text{(Expression 1)}$$

Figure 5:
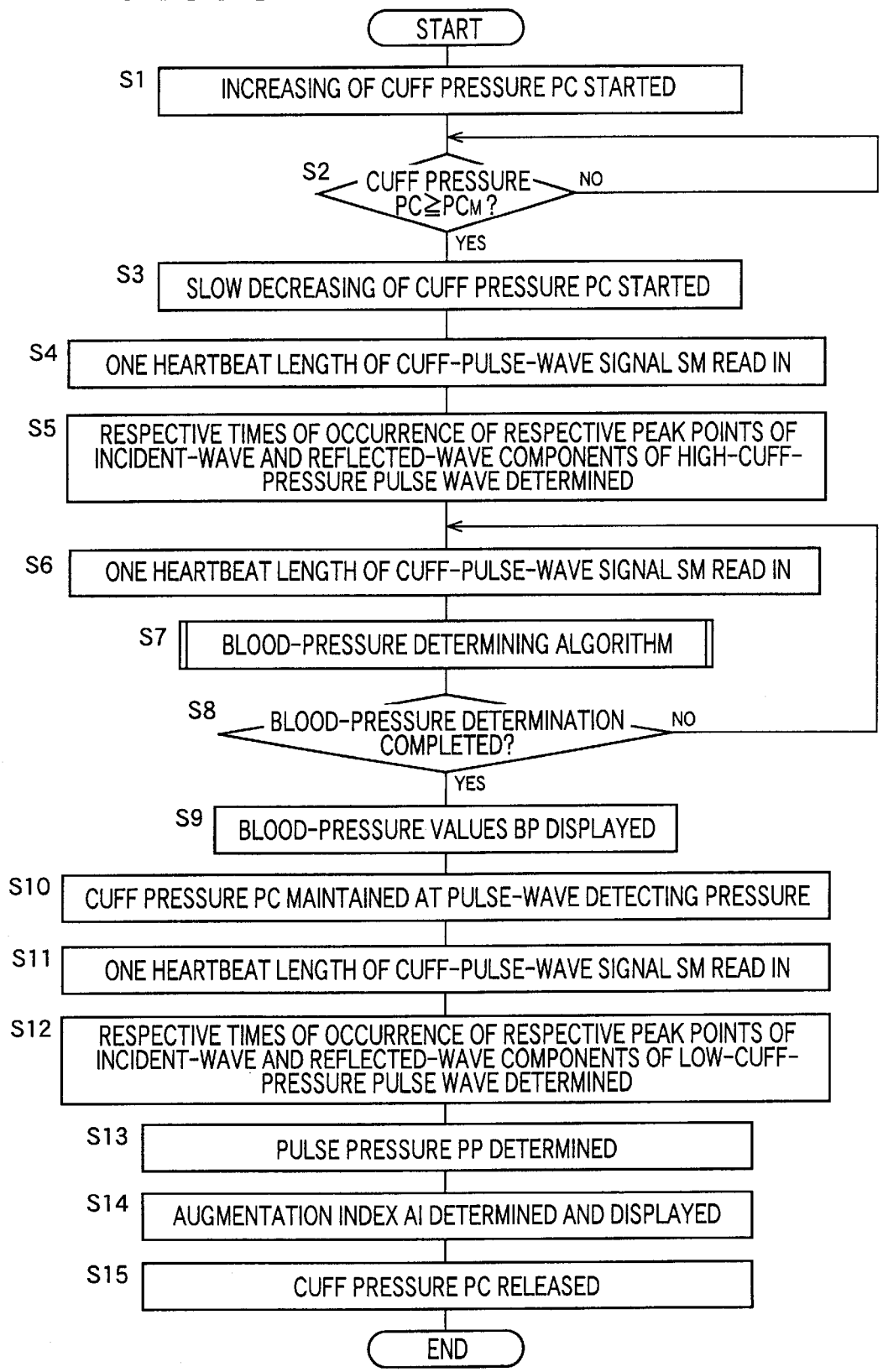
FIG. 5 is a flow chart for explaining more concretely the control functions of a CPU (central processing unit) of the control device, shown in FIG. 3.

FIG. 5 is a flow chart representing the control functions of the CPU 36, shown in the diagrammatic view of FIG. 3.

In FIG. 5, first, at Step S1 (hereinafter, the term "Step(s)" is omitted), the CPU starts the air pump 24 and operates the pressure control valve 18 so as to start quickly increasing the cuff pressure PC. Subsequently, at S2, the CPU judges whether the cuff pressure PC has exceeded an increase-target pressure $PC_M$ that is pre-set at 180 mmHg higher than a systolic blood pressure $BP_{SYS}$ of the upper arm 14. S2 is repeated until a positive judgment is made, while the cuff pressure PC is quickly increased. Meanwhile, if a positive judgment is made at S2, the control goes to S3 to stop the air pump 24 and operate the pressure control valve 18 so as to start slowly decreasing the cuff pressure PC at a rate of about 3 mmHg/sec.

Subsequently, at S4, the CPU reads in one heartbeat-synchronous pulse of the cuff-pulse-wave signal SM supplied from the pulse-wave filter circuit 28. Since the pulse wave represented by the cuff-pulse-wave signal SM read in at S4 is one that is detected just after the commencement of the slow decreasing of the cuff pressure PC, the pulse wave is a high-cuff-pressure pulse wave that is detected in a state in which the cuff pressure is higher than the systolic blood pressure $BP_{SYS}$ of the upper arm 14.

Next, the control goes to S5 corresponding to the peak-occurrence-time determining means 54. At S5, the CPU determines respective times of occurrence of respective peak points of incident-wave and reflected-wave components of the high-cuff-pressure pulse wave read in at S4. Since the high-cuff-pressure pulse wave has two maximal points, as indicated at one-dot-chain line in FIGS. 4A and 4B, the CPU determines a time of occurrence of the earlier one of the two maximal points as the time of occurrence of the peak point of the incident-wave component of the high-cuff-pressure pulse wave, and additionally determines a time of occurrence of the later one of the two maximal points as the time of occurrence of the peak point of the reflected-wave component of the high-cuff-pressure pulse wave.

Then, the control goes to S6 to S9 corresponding to the blood-pressure determining means 52. At S6, the CPU carries out the same operation as that carried out at S4, i.e., reads in one heartbeat-synchronous pulse of the cuff-pulse-wave signal SM supplied from the pulse-wave filter circuit 28. Subsequently, at S7, the CPU determines, based on change of respective amplitudes of successive heartbeat-synchronous pulses of the brachial pulse wave represented by the cuff-pulse-wave signal SM successively obtained at S6 during the slow decreasing of the cuff pressure PC, a systolic blood pressure $BP_{SYS}$, a mean blood pressure $BP_{MEAN}$, and a diastolic blood pressure $BP_{DIA}$ of the patient, according to well-known oscillometric blood-pressure determining algorithm. Then, at S8, the CPU judges whether the determination of the blood-pressure values BP has completed at S7. Since the diastolic blood pressure $BP_{DIA}$ is last determined at S7, the CPU judges, at S8, whether the diastolic blood pressure $BP_{DIA}$ has been determined. S6 and the following steps are repeated until a positive judgment is made at S8, while the blood-pressure determining algorithm is continued. Meanwhile, if a positive judgment is made at S8, the control goes to S9 to operate the display device 42 to display the systolic, mean, and diastolic blood-pressure values $BP_{SYS}$, $BP_{MEAN}$, $BP_{DIA}$ determined at S7.

Then, at S10, the CPU determines a pulse-wave detecting pressure by subtracting a prescribed, considerably small value, α, from the diastolic blood-pressure value $BP_{DIA}$ determined at S7, and operates, when the cuff pressure PC is decreased down to the thus determined pulse-wave detecting pressure, the pressure control valve 18 to maintain the cuff pressure PC at the pulse-wave detecting pressure.

Next, at S11, the CPU carries out the same operation as that carried out at S4 or S6, i.e., reads in one heartbeat-synchronous pulse of the cuff-pulse-wave signal SM supplied from the pulse-wave filter circuit 28 in the state in which the cuff pressure PC is maintained at the pulse-wave detecting pressure. Since the pulse wave represented by the cuff-pulse-wave signal SM read in at S11 is one that is detected in the state in which the cuff pressure PC is lower than the diastolic blood pressure $BP_{SYS}$ of the upper arm 14, the pulse wave is a low-cuff-pressure pulse wave.

Then, the control goes to S12 to S14 corresponding to the augmentation-index determining means 56. First, at S12, the CPU determines a rising point of the high-cuff-pressure pulse wave read in at S4, and determines a first time duration between a time of occurrence of the rising point and the time of occurrence of the peak point of the incident-wave component determined at S5, and a second time duration between the time of occurrence of the rising point and the time of occurrence of the peak point of the reflected-wave component also determined at S5. In addition, the CPU determines a rising point of the low-cuff-pressure pulse wave read in at S11, and determines, as a time of occurrence of a peak point of an incident-wave component of the low-cuff-pressure pulse wave, a time subsequent from the rising point by the first time duration, and additionally determines, as a time of occurrence of a peak point of a reflected-wave component of the low-cuff-pressure pulse wave, a time subsequent from the rising point by the second time duration. Since, in the graphs shown in FIGS. 4A and 4B, the respective rising points of the high-cuff-pressure pulse wave and the low-cuff-pressure pulse wave are aligned with each other, the respective times of occurrence of the respective peak points of the incident-wave and reflected-wave components of the high-cuff-pressure pulse wave are determined as the respective time of occurrence of the respective peak points of the incident-wave and reflected-wave components of the low-cuff-pressure pulse wave.

Next, at S13, the CPU determines, as a pulse pressure PP of the low-cuff-pressure pulse wave, a difference obtained by subtracting the smallest magnitude of the one heartbeat-synchronous pulse of the cuff-pulse-wave signal SM read in at S11, from the greatest magnitude of the same pulse. Then, at S14, the CPU determines a difference ΔP by subtracting a magnitude, a, of the low-cuff-pressure pulse wave at the time of occurrence of the peak point of the incident-wave component thereof, from a magnitude, b, thereof at the time of occurrence of the peak point of the reflected-wave component thereof, and substitutes, for the above-indicated Expression 1, the difference ΔP and the pulse pressure PP determined at S13, so as to determine an augmentation index AI, and additionally operates the display device 42 to display the thus determined index AI.

Then, at S15, the CPU operates the pressure control valve 18 to decrease the cuff pressure PC to an atmospheric pressure.

In the embodiment employing the above-described flow chart, the control device 32 determines, at S5 (the peak-occurrence-time determining means 54), the respective times of occurrence of the respective peak points of the incident-wave and reflected-wave components of the brachial pulse wave detected in the state in which the cuff pressure PC is higher than the systolic blood pressure $BP_{SYS}$ of the patient, additionally determines, at S12 to S14 (the augmentation-index determining means 56), the respective times of occurrence of the respective peak points of the incident-wave and reflected-wave components of the low-cuff-pressure pulse wave, based on the respective times of occurrence of the respective peak points of the incident-wave and reflected-wave components, determined at S5 (the peak-occurrence-time determining means 54), and finally determines the augmentation index AI based on the respective magnitudes of the low-cuff-pressure pulse wave at the respective times of occurrence of the respective peak points of the incident-wave and reflected-wave components thereof. The thus determined augmentation index enjoys a high accuracy.

In addition, in the embodiment employing the above-described flow chart, the control device 32 obtains the high-cuff-pressure pulse wave and the low-cuff-pressure pulse wave, while the cuff pressure PC is changed in the blood-pressure measuring operation, and determines the augmentation index AI based on the thus obtained high-cuff-pressure and low-cuff-pressure pulse waves. Thus, the control device 32 concurrently obtains the blood-pressure values BP and the augmentation index AI.

While the present invention has been described in its preferred embodiment by reference to the drawings, it is to be understood that the invention may otherwise be embodied.

For example, in the illustrated arteriosclerosis inspecting apparatus 10, the cuff 12 is worn on the upper arm 14 of the patient. However, the cuff 12 may be worn on a different portion of the patient, such as a femoral portion or an ankle.

In addition, in the illustrated arteriosclerosis inspecting apparatus 10, the cuff-pressure changing means 50 slowly decreases the cuff pressure PC immediately after having increased the cuff pressure PC up to the pressure higher than the systolic blood pressure $BP_{SYS}$ of the upper arm 14, and the control device 32 obtains, as the high-cuff-pressure pulse wave, the brachial pulse wave detected during the slow decreasing of the cuff pressure PC. On the other hand, the control device 32 obtains, as the low-cuff-pressure pulse wave, the brachial pulse wave detected in the state in which the cuff pressure PC is maintained at the pulse-wave detecting pressure. However, the cuff-pressure changing means 50 may be modified to maintain the cuff pressure PC at a pressure higher than the systolic blood pressure $BP_{SYS}$ of the upper arm 14, and the control device 32 may be modified to obtain, as the high-cuff-pressure pulse wave, a brachial pulse wave detected in the state in which the cuff pressure PC is maintained at that pressure. In addition, the control device 32 may be modified to obtain, as the low-cuff-pressure pulse wave, a brachial pulse wave detected during a slow decreasing of the cuff pressure PC.

Moreover, in the illustrated arteriosclerosis inspecting apparatus 10, the control device 32 obtains, as the high-cuff-pressure pulse wave, the brachial pulse wave detected immediately after the commencement of the slow decreasing of the cuff pressure PC from the prescribed increase-target pressure $PC_M$. Thus, the cuff pressure PC at which the high-cuff-pressure pulse wave is detected is a prescribed pressure. However, it is possible to actually measure a systolic blood pressure $BP_{SYS}$ of the patient and determine, based on the measured systolic blood pressure $BP_{SYS}$, a cuff pressure PC at which a high-cuff-pressure pulse wave is to be detected.

On the other hand, in the illustrated arteriosclerosis inspecting apparatus 10, the cuff pressure PC at which the low-cuff-pressure pulse wave is detected is determined based on the actually measured blood pressure BP. However, the cuff pressure PC at which the low-cuff-pressure pulse wave is detected may be a prescribed pressure or may be a pressure within a prescribed pressure range.

Generally, the denominator of the fraction (Expression 1) used to determine the augmentation index is the pulse pressure PP. However, the pulse pressure PP of Expression 1 may be replaced with the amplitude (i.e., the magnitude) of the low-cuff-pressure pulse wave at the time of occurrence of the peak point of the incident-wave component thereof or the reflected-wave component thereof, because the fraction having the amplitude as the denominator indicates arteriosclerosis.

The present invention may be embodied with other various changes without departing from the spirit of the invention.

What is claimed is:

1. An apparatus for determining, based on a pulse wave detected from a living subject, an augmentation index indicating a proportion of a reflected-wave component of the pulse wave to an incident-wave component thereof, the apparatus comprising:

an inflatable cuff which is adapted to be worn on a portion of the subject and inflated to apply a pressing pressure to said portion;

a cuff-pressure changing device which changes the pressing pressure of the cuff;

a pulse-wave extracting device which extracts a pulse wave from a pressure oscillation which is transmitted from said portion of the subject to the cuff;

a peak-occurrence-time determining means for determining, based on a high-cuff-pressure pulse wave which is extracted by the pulse-wave extracting device when the cuff-pressure changing device makes the pressing pressure of the cuff higher than a systolic blood pressure of said portion of the subject, a time of occurrence of a peak point of an incident-wave component of the high-cuff-pressure pulse and a time of occurrence of a peak point of a reflected-wave component of the high-cuff-pressure pulse wave; and an augmentation-index determining means for determining, based on the respective times of occurrence of the respective peak points of the incident-wave and reflected-wave components of the high-cuffpressure pulse, determined by the peak-occurrence-time determining means, respective times of occurrence of respective peak points of incident-wave and reflected-wave components of a low-cuff-pressure pulse which is extracted by the pulse-wave extracting device when the cuff-pressure changing device makes the pressing pressure of the cuff lower than a mean blood pressure of said portion of the subject, and determining an augmentation index based on respective magnitudes of the low-cuff-pressure pulse wave at the respective times of occurrence of the respective peak points of the incident-wave and reflected-wave components of the low-cuff-pressure pulse.

2. An apparatus according to claim 1, wherein the cuff is adapted to be worn on an upper arm of the subject, and wherein the augmentation-index determining means determines the augmentation index based the high-cuff-pressure pulse wave and the low-cuff-pressure pulse wave each of which is extracted by the pulse-wave extracting device from the pressure oscillation transmitted from an artery of the upper arm to the cuff worn on the upper arm.

3. An apparatus according to claim 1, wherein the cuff-pressure changing device decreases, in a blood-pressure measuring operation, the pressing pressure of the cuff from a pressure higher than the systolic blood pressure of said portion of the subject, to a pressure lower than a diastolic blood pressure of said portion of the subject, wherein the pulse-wave extracting device extracts the high-cuff-pressure pulse wave when the cuff-pressure changing device makes, in the blood-pressure measuring operation, the pressing pressure of the cuff higher than the systolic blood pressure of said portion of the subject, and wherein the pulse-wave extracting device extracts the low-cuff-pressure pulse wave when the cuff-pressure changing device makes, in the blood-pressure measuring operation, the pressing pressure of the cuff lower than the diastolic systolic blood pressure of said portion of the subject.

4. An apparatus for inspecting arteriosclerosis of the living subject, based on the augmentation index determined by the apparatus according to claim 1.

5. An apparatus according to claim 4, further comprising a display device which displays the augmentation index so that the augmentation index is read by a person to inspect the arteriosclerosis of the subject.

6. An apparatus according to claim 3, further comprising a blood-pressure determining means for determining at least one blood-pressure value of the subject based on change of respective amplitudes of successive heartbeat-synchronous pulses of the pulse wave extracted by the pulse-wave extracting device while the cuff-pressure changing device decreases the pressing pressure of the cuff from a pressure which is higher than the systolic blood pressure of said portion of the subject, to a pressure which is lower than the diastolic blood pressure of said portion of the subject.

7. An apparatus according to claim 1, wherein the augmentation-index determining means comprises:

first means for determining a first difference between the respective magnitudes of the low-cuff-pressure pulse wave at the respective times of occurrence of the respective peak points of the incident-wave and reflected-wave components of the low-cuff-pressure pulse; and second means for determining the augmentation index based on the first difference.

8. An apparatus according to claim 7, wherein the augmentation-index determining means further comprises third means for determining a second difference between a smallest magnitude and a greatest magnitude of the low-cuff-pressure pulse wave, and wherein the second means determines the augmentation index based on a value obtained by dividing the first difference by the second difference.

* * * * *